(12) United States Patent
Kunitsky et al.

(10) Patent No.: US 7,468,415 B2
(45) Date of Patent: Dec. 23, 2008

(54) METHOD FOR PREPARING GLYCIDYLOXYSTYRENE MONOMERS AND POLYMERS THEREOF

(75) Inventors: Keith Kunitsky, West Grove, PA (US); Mukesh C. Shah, Hockessin, DE (US); Steven W. Shuey, Landenberg, PA (US); Mark E. Wagman, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/961,093

(22) Filed: Dec. 20, 2007

(65) Prior Publication Data

US 2008/0167433 A1    Jul. 10, 2008

Related U.S. Application Data

(60) Provisional application No. 60/883,358, filed on Jan. 4, 2007.

(51) Int. Cl.
*C08F 2/00* (2006.01)
*C07D 301/28* (2006.01)
*C08F 12/22* (2006.01)

(52) U.S. Cl. .................. 526/75; 526/273; 549/516
(58) Field of Classification Search .......... 568/654; 526/75, 273; 549/516
See application file for complete search history.

(56) References Cited

U.S. PATENT DOCUMENTS

| 3,014,890 | A | | 12/1961 | Bradiey et al. | |
|---|---|---|---|---|---|
| 3,431,246 | A | * | 3/1969 | Vecellio | 526/225 |
| 4,696,988 | A | * | 9/1987 | Higashimura et al. | 526/220 |
| 5,084,490 | A | * | 1/1992 | McArdle et al. | 522/181 |
| 5,274,060 | A | | 12/1993 | Schadeli | |
| 6,225,385 | B1 | | 5/2001 | Stahrfeldt et al. | |
| 2005/0228191 | A1 | * | 10/2005 | Kunitsky et al. | 560/130 |

OTHER PUBLICATIONS

Hashimoto et al., Selective Vinyl Cationic Polymerization of Monomers With Two Cationically Polymerizable Groups. II. P-Vinylphenyl Glycidyl Ether: An Epoxy-Functionalized Styrene, J. of Polymer Science, Part A: Polymer Chemistry, 1987, vol. 25:2827-2838.

Tanimoto et al., Synthesis of Some New Polymers From p-Vinylphenol, J. Syn. Org. Chem. JPN., 1968, vol. 26:1102-1106.

Tanaka, Self-Cross Linkable Polyepoxides, ACS Symposium Series, 1979, vol. 114:197-210.

Pyysalo et al., The Thermal Decarboxylation of Some Substituted Cinnamic Acids, Food Science & Technology, 1977, vol. 10:145-147.

Cohen et al., A Study of PH Dependence in The Decarboxylation of P-Hydroxycinnamic Aicid, J. Amer. Chem. Soc., 1960, vol. 82:1907-1911.

* cited by examiner

*Primary Examiner*—Fred M Teskin

(57) ABSTRACT

It was found that glycidyloxystyrenes, including glycidyloxystyrene and substituted glycidyloxystyrene, can be synthesized from hydroxycinnamic acid or substituted hydroxycinnamic acids in a one-pot, two-step process. The substrate can be thermally decarboxylated and then without purification, reacted in the presence of a halomethyl-oxirane and a base. The resulting product can be polymerized or coppolymerized to a fully substituted product.

19 Claims, No Drawings

METHOD FOR PREPARING GLYCIDYLOXYSTYRENE MONOMERS AND POLYMERS THEREOF

This application claims the benefit of U.S. Provisional Application 60/883,358, filed Jan. 4, 2007.

FIELD OF INVENTION

The invention relates to the field of organic synthesis. More specifically, the invention relates to a method for preparing glycidyloxystyrenes from substituted hydroxycinnamic acids in a one-pot process, and subsequent polymerization of the resulting monomer.

BACKGROUND OF THE INVENTION

Para-glycidyloxystyrene (pGS) is a monomer with great versatility and utility due to its epoxy functionality and its superior thermal, chemical, and hydrolytic resistance relative to the most commonly used epoxy-containing vinylic monomer, glycidyl methacrylate. The epoxy functionality is highly useful for curing and adhesion. For example, pGS monomer may be used as a functional component of coatings, adhesives, films, plastics, resins, elastomers, automotive finishes and inks, as well as in electronic materials. Also homopolymers or copolymers of pGS will provide materials with advantages in performance and versatility.

A number of methods for the chemical synthesis of pGS are known. However, these methods require starting materials that are difficult to prepare and are not commercially available, are expensive, and/or require multiple steps. For example, U.S. Pat. No. 6,255,385 discloses a two-step process for the synthesis of pGS starting from 4-hydroxybenzaldehyde, with an overall 20% yield for the two steps. IT705414 discloses the synthesis of pGS also starting with 4-hydroxybenzaldehyde, in which multiple steps were required to synthesize the para-hydroxystyrene intermediate, which is purified prior to further reaction. The conversion of para-hydroxystyrene to pGS is performed with a strong excess of epichlorohydrin in the virtual absence of water, with continuous distillation to remove water as it forms in the reaction. A one-step process for the synthesis of pGS starting from acetoxystyrene is described in Hashimoto ((1987) J of Polymer Science, Part A:Polymer Chemistry 25:2827-2838). The cost of acetoxystyrene makes this method commercially unattractive.

Though pGS has been made from p-hydroxystyrene (pHS), pHS is available commercially only in small quantities, and is available in a form unsuitable for glycidyloxylation (in 10% ethylene glycol) or as pure pHS, which is fairly unstable and very costly. U.S. Pat. No. 5,274,060 describes a method for preparing 4-hydroxystyrene starting with pHCA. In that method, the pHCA is decarboxylated in dimethyl sulfoxide in the presence of an amine catalyst, i.e., 1,8-diazabicyclo[5,4-0]undec-7-ene, and hydroquinone at 135° C. to give 4-hydroxystyrene. The yield in that method was 63%.

Monomers of pGS have been polymerized with AIBN as initiator at 80° C. (Tanimoto et al. (1968) J. Syn. Org. Chem. Jpn. 26:1102-1106), or by cationic initiators with selective polymerization of the vinyl group and not the epoxide using HI/I$_2$ (Hashimoto et al., (1987) J. Poly. Sci. Part A Polym. Chem. 25: 2827-2838). Also pGS was copolymerized with vinylpyridines at 60° C. in THF initiated by AIBN (Tanaka (1979) ACS Symposium Series 114 (epoxy resin chemistry): 197-210).

The thermal decarboxylation of substituted cinnamic acids has been studied in aqueous media. Pyysalo et al. (*Lebensmittel-Wissenschraft u. Technol.* 10 (Food Science and Technology):145-147 (1977)) describe the thermal decarboxylation of substituted cinnamic acid derivatives at pH 1 to 6 at 100° C. in aqueous buffer. Cohen et al. (*J. Amer. Chem. Soc.* 82:1907-1911 (1960)) describe the thermal decarboxylation of p-hydroxycinnamic acid in aqueous buffers at pH 1 to 12.

Thermal, base-catalyzed decarboxylation of phenolic substrates followed by acetylation in a single reaction vessel, two-step process is disclosed in US 20050228191.

The need exists for a method for preparing GS monomers and polymers thereof that uses relatively inexpensive reagents, is relatively simple, and results in high yields. Applicants have solved the stated problem by discovering a simple method for preparing pGS starting with para-hydroxycinnamic acid (pHCA) which involves an HSM intermediate that does not require isolation.

SUMMARY OF THE INVENTION

The invention relates to a method for the synthesis of glycidyloxystyrene, or substituted glycidyloxystyrenes, from hydroxycinnamic acid or substituted hydroxycinnamic acids, which may be performed in a single reaction vessel with no need for purification of any intermediates. The substrate is first thermally decarboxylated in the presence of a non-amine basic catalyst, and the resulting unpurified product is then converted to a GS in the presence of a halomethyl-oxirane and a base.

Accordingly it is within the scope of the invention to provide a method for the synthesis of a glycidyloxystyrene monomer or a substituted glycidyloxystyrene monomer comprising the steps of:

a) providing a phenolic substrate having the general structure:

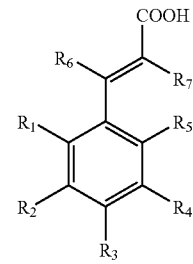

wherein $R_1$, $R_2$, $R_3$, $R_4$, and $R_5$ are H, OH, OCH$_3$, OR$_8$, or linear or branched alkyl, aryl, halo, or cyano; $R_6$ and $R_7$ are H, halo, or cyano; $R_8$ is linear or branched alkyl or aryl; provided that at least one of $R_1$, $R_3$, or $R_5$ is OH;

b) providing a reaction mixture comprising:
  i) a non-amine basic catalyst; and
  ii) at least one aprotic, polar solvent;

c) contacting the phenolic substrate of (a) with the reaction mixture of (b) at a temperature of at least about 100° C. for a time sufficient for the decarboxylation of the phenolic substrate to a decarboxylated product;

d) contacting the decarboxylated product of (c) with a halomethyl-oxirane and a basic catalyst at a temperature between about 20° C. and about 120° C. for a time sufficient for glycidyloxystyrene monomer or substituted glycidyloxystyrene monomer synthesis; and e) optionally recovering the glycidyloxystyrene monomer or substituted glycidyloxystyrene monomer.

In another embodiment the invention provides a method for the synthesis of homopolymers and copolymers of glycidyloxystyrene monomer or substituted glycidyloxystyrene monomer comprising:
a) providing a phenolic substrate having the general structure:

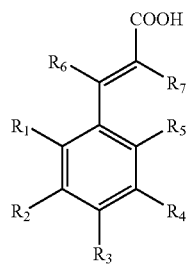

wherein $R_1$, $R_2$, $R_3$, $R_4$, and $R_5$ are H, OH, OCH$_3$, OR$_8$, or linear or branched alkyl, aryl, halo, or cyano; $R_6$ and $R_7$ are H, halo, or cyano; $R_8$ is linear or branched alkyl or aryl; provided that at least one of $R_1$, $R_3$, or $R_5$ is OH;
b) providing a reaction mixture comprising:
   i) a non-amine basic catalyst; and
   ii) at least one aprotic, polar solvent;
c) contacting the phenolic substrate of (a) with the reaction mixture of (b) at a temperature of at least about 100° C. for a time sufficient for the decarboxylation of the phenolic substrate to a decarboxylated product;
d) contacting the decarboxylated product of (c) with a halomethyl-oxirane and a basic catalyst at a temperature between about 20° C. and about 120° C. for a time sufficient for glycidyloxystyrene monomer or substituted glycidyloxystyrene monomer synthesis;
e) optionally recovering the glycidyloxystyrene monomer or substituted glycidyloxystyrene monomer; and
f) reacting the glycidyloxystyrene monomer or substituted glycidyloxystyrene monomer, with optionally at least one co-monomer, with a polymerization initiator at a temperature and time sufficient to produce a glycidyloxystyrene homopolymer or copolymer, or substituted glycidyloxystyrene homopolymer or copolymer.

In an additional embodiment of the invention, a composition comprising a glycidyloxystyrene homopolymer or copolymer, or substituted glycidyloxystyrene homopolymer or copolymer prepared according to the instant method is provided.

DETAILED DESCRIPTION OF THE INVENTION

The invention provides a method for synthesizing glycidyloxystyrenes, including substituted glycidyloxystyrenes, via a thermal, non-amine base-catalyzed decarboxylation of hydroxycinnamic acids (HCA) or substituted hydroxycinnamic acids, followed directly by treatment with a halomethyl-oxirane and base. The method is useful because glycidyloxystyrenes may be used as functional components of films, plastics, resins, elastomers, adhesives, coatings, automotive finishes, inks and electronic materials. Also homopolymers or copolymers of glycidyloxystyrenes provide materials with advantages in performance and versatility for many applications such as in chemically, thermally, and abrasion resistant coatings.

The following definitions are used herein and should be referred to for interpretation of the claims and the specification.

"p" means para.

"pGS" means p-glycidyloxystyrene.

"pHS" is the abbreviation used for para-hydroxystyrene which is also represented as p-hydroxystyrene or 4-hydroxystyrene.

"HSM" means hydroxystyrenes, which includes pHS and substituted hydroxystyrene monomer.

"pHCA" is the abbreviation used for para-hydroxycinnamic acid which is also represented as p-hydroxycinnamic acid or 4-hydroxy cinnamic acid.

"HCA" means hydroxycinnamic acids, which includes pHCA and substituted hydroxycinnamic acid.

"CA" means cinnamic acids, which includes substituted cinnamic acids.

The term "glycidyloxystyrenes" or "GS" as used herein refers to glycidyloxystyrene and substituted glycidyloxystyrene having the general structure:

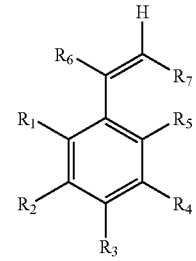

wherein $R_1$, $R_2$, $R_3$, $R_4$, and $R_5$ are glycidyloxy, H, OCH$_3$, OH, OR$_8$, or linear or branched alkyl, aryl, halo, or cyano; $R_6$ and $R_7$ are H, halo, or cyano; $R_8$ is linear or branched alkyl or aryl; provided that at least one of $R_1$, $R_2$, $R_3$, $R_4$, or $R_5$ is glycidyloxy.

The term "GS product" refers to at least one type of GS that is produced using the present process.

The term "yield" as used herein refers to the amount of product produced in a chemical reaction. The yield is typically expressed as a percentage of the theoretical yield for the reaction. The term "theoretical yield" means the predicted amount of product to be expected based on the amount of substrate initially present and the stoichiometry of the reaction.

The term "polar" as applied to solvents of the invention refers to solvents characterized by molecules having sizable permanent dipole moments.

The term "aprotic" as applied to the solvents of the invention refers to a solvent that is incapable of acting as a labile proton donor or acceptor.

The term "protic" as applied to the solvents of the invention refers to a solvent that is capable of acting as a labile proton donor or acceptor.

The term "polar organic solvent mixture" refers to a mixture of organic solvents comprising at least one polar solvent.

The term "aprotic, polar organic solvent mixture" refers to a mixture of organic solvents comprising at least one aprotic, polar solvent.

"TAL" is the abbreviation used for tyrosine ammonia lyase.

"PAH" is the abbreviation used for phenylalanine hydroxylase.

The term "TAL activity" refers to the ability of a protein to catalyze the direct conversion of tyrosine to pHCA.

All ranges given herein include the end of the ranges and also all the intermediate range points.

In one embodiment, the instant invention provides a method for producing glycidyloxystyrenes in monomer form. Depending on the specific structure of the specific hydroxycinnamic acid (HCA), which may be a substituted hydroxycinnamic acid, substrate used in the present method, the glycidyloxystyrene product may be para- and/or ortho-glycidyloxystyrene. In addition to para- and/or ortho-, the product may be meta-glycidyloxystyrene. The glycidyloxystyrene product may be derived from any available HCA substrate that includes a hydroxy group in the para and/or ortho position. Substituted glycidyloxystyrenes are produced when the starting hydroxycinnamic acid contains functional groups in addition to the phenolic group in the orho or para position. For example, starting with 3-methoxy-4-hydroxy cinnamic acid (ferulic acid), one obtains 4-glycidyloxy, 3-methoxystyrene as the product. When the other functional groups are reactive with halomethyloxiranes, products with more than one glycidyloxy group are obtained. For example, 3,4,diglycidyloxystyrene is obtained when the starting material is 3,4,-dihydroxycinnamic acid (caffeic acid).

Examples of GS monomers that may be produced by the present method include, but are not limited to compounds having the following structures:

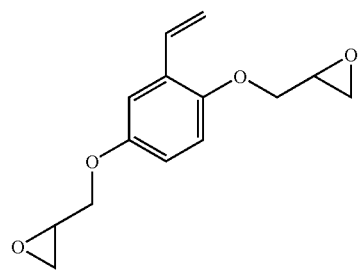

-continued

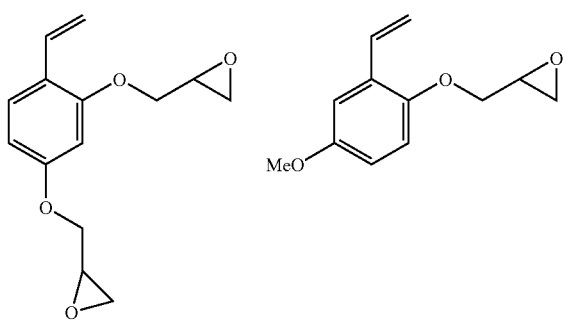

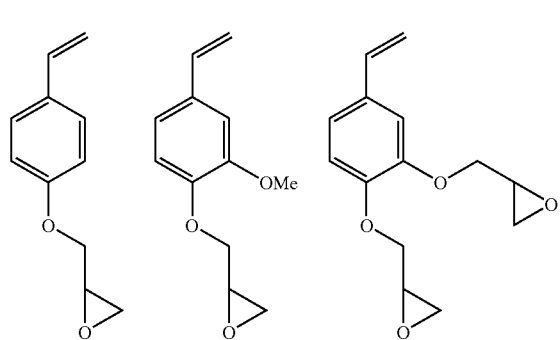

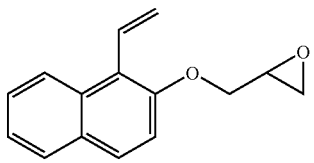

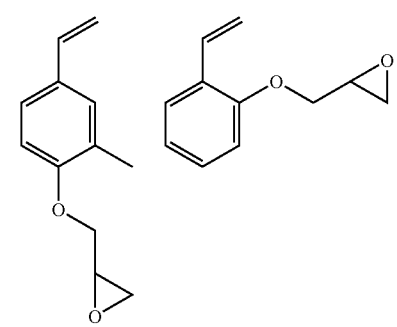

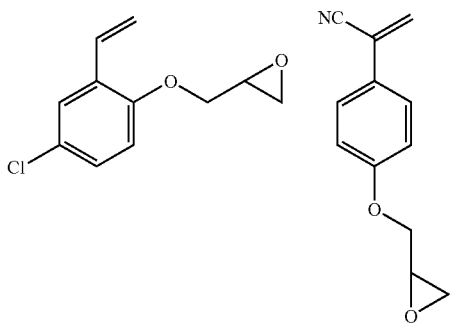

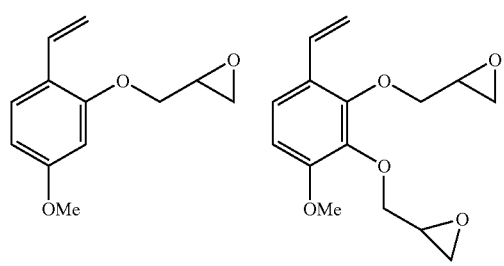

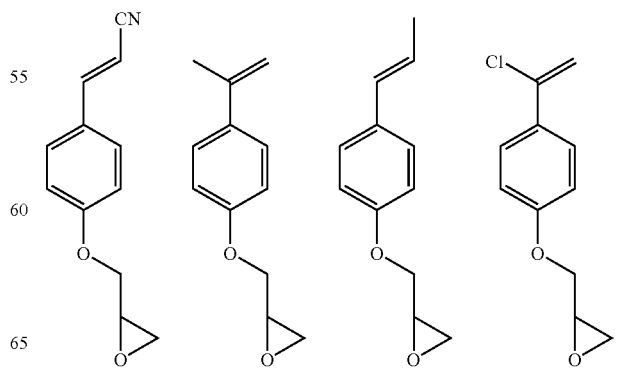

-continued

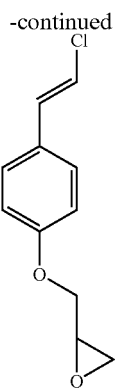

In a second embodiment, the instant invention provides a method for producing polymers or copolymers of glycidyloxystyrenes. Any of the glycidyloxystyrene monomers produced in the present method may be polymerized without or with additional types of monomers, as described below.

Phenolic Substrates

The hydroxycinnamic acids (HCA), including substituted hydroxycinnamic acids, used as substrates in the present method are phenolic compounds with the general structure:

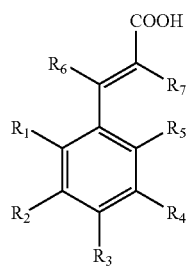

wherein $R_1$, $R_2$, $R_3$, $R_4$, and $R_5$ are H, OH, $OCH_3$, $OR_8$, or linear or branched alkyl, aryl, halo, or cyano; $R_6$ and $R_7$ are H, halo, or cyano; $R_8$ is linear or branched alkyl or aryl; provided that at least one of $R_1$, $R_3$, or $R_5$ is OH.

Examples of suitable phenolic substrates include, but are not limited to 4-hydroxycinnamic acid, ferulic acid, sinapinic acid, caffeic acid, 2-hydroxycinnamic acid, and α-cyano-4-hydroxycinnamic acid. As described in commonly owned and co-pending U.S. patent application 60/556,861, which is herein incorporated by reference, high yields of the decarboxylated product may be obtained even with non-sterically hindered phenol substrates, which are more prone to product decomposition than sterically hindered phenols. Sterically hindered phenols are herein defined as phenols having large, bulky groups, such as t-butyl, at both $R_2$ and $R_4$ positions. Non-sterically hindered phenols are phenols that do not have large, bulky groups at both $R_2$ and $R_4$ positions. Non-sterically hindered phenol substrates include, but are not limited to, phenols wherein at least one of $R_2$ or $R_4$ is H, OH, $OCH_3$, methyl, ethyl, or propyl. Moreover, high yields of decarboxylated product may be obtained even with ortho unsubstituted phenol substrates, which are also prone to product decomposition. Ortho unsubstituted phenols are herein defined as phenols wherein at least one of $R_2$ or $R_4$ is H.

These phenolic substrates may be obtained in a number of ways. For example, 4-hydroxycinnamic acid (pHCA), predominantly in the trans form, is available commercially from companies such as Aldrich (Milwaukee, Wis.) and TCI America (Portland, Oreg.). Additionally, pHCA may be prepared by chemical synthesis using any method known in the art. For example, pHCA may be obtained by reacting malonic acid with para-hydroxybenzaldehyde as described by Pittet et al. in U.S. Pat. No. 4,316,995, or by Alexandratos in U.S. Pat. No. 5,990,336. Alternatively, pHCA may also be isolated from plants (R. Benrief et al. *Phytochemistry* 47:825-832 (1998) and U.S. Patent Application Publication No. 20020187207). In addition, pHCA may be from bioproduction using a microbial production host. The production host may be one or more recombinant host cell, which is prepared using standard genetic engineering techniques. These recombinant DNA techniques are described by Sambrook, J., Fritsch, E. F. and Maniatis, T. *Molecular Cloning: A Laboratory Manual*, Second Edition, Cold Spring Harbor Laboratory Press, Cold Spring Harbor, N.Y. (1989), incorporated herein by reference.

An example of bioproduction of pHCA is as described by Qi et al. in U.S. Patent Application Publication No. 20030079255, incorporated herein by reference. According to that disclosure, pHCA may be produced using a recombinant microorganism engineered to express at least one gene encoding a phenylalanine hydroxylase (PAH) activity and at least one gene encoding a tyrosine ammonia lyase (TAL) activity. This transformed microorganism metabolizes a fermentable carbon source, such as glucose, to phenylalanine, which is converted to tyrosine by PAH. The tyrosine produced is converted to pHCA by the TAL enzyme. Another example is pHCA is production using a two-stage fermentation as described by Ben-Bassat in copending and commonly owned U.S. Patent Application No. 60/563,633, incorporated herein by reference. The first stage comprises providing a microbial production host having an enhanced ability to produce the aromatic amino acid tyrosine (an over-producer). These cells are grown at physiological pH to a point where tyrosine is accumulated in the growth medium. During the second stage of the fermentation the cells are contacted with a source of TAL at a pH of about 8.0 to about 11.0. During this stage tyrosine is converted to pHCA at relatively high rates and yields. Alternatively, the two stages may be done as two separate steps, wherein the tyrosine is isolated from the fermentation medium of the first step and then is contacted with the source of TAL.

Additional substrates such as ferulic acid, sinapinic acid, and caffeic acid are available commercially from companies such as Aldrich (Milwaukee, Wis.) and TCI America (Portland, Oreg.). Alternatively as these substrates are all natural plant products, comprising elements of the lignin biosynthetic pathway, they may be readily isolated from plant tissue (see for example Jang et al., *Archives of Pharmacal Research* (2003), 26(8), 585-590; Matsufuji et al., *Journal of Agricultural and Food Chemistry* (2003), 51(10), 3157-3161; WO 2003046163; Couteau et al, *Bioresource Technology* (1998), 64(1), 17-25; and Bartolome et al., *Journal of the Science of Food and Agriculture* (1999), 79(3), 435-439). Additionally, methods of chemical synthesis are known for a number of the more common phenolic substrates (see for example WO 2002083625 ("Preparation of ferulic acid dimers and their pharmaceutically acceptable salts, and use thereof for treating dementia") JP 2002155017 ("Preparation of caffeic acid from ferulic acids"); and Taniguchi et al., *Anticancer Research* (1999), 19(5A), 3757-3761). The preparation of alkylated pHCA derivatives is described by Lala et al. in Australian Patent Application No. 7247129.

Non-amine Basic Catalysts

The method of the invention makes use of a non-amine basic catalyst. A non-amine basic catalyst is any basic compound capable of facilitating the present reactions that does not contain amines. By way of comparison examples of amine containing catalysts are pyridine and ethylenediamine. Virtually any non-amine basic catalyst may be used that is compatible with the reaction conditions of the invention, where metallic salts and particularly potassium salts or acetate salts are preferred. Catalysts particularly suitable in the present invention include, but are not limited to, potassium acetate, potassium carbonate, potassium hydroxide, sodium acetate, sodium carbonate, sodium hydroxide and magnesium oxide. The non-amine catalysts used in the present method are available commercially from, for example, EM Science (Gibbstown, N.J.) or Aldrich (Milwaukee, Wis.).

The optimum concentration of non-amine basic catalyst will vary depending on the concentration of substrate, nature of the solvent used and reaction conditions. Typically concentrations of about 1 mol % to about 30 mol %, relative to the substrate, in the reaction mixture are preferred.

Organic Solvents

In the present method, a wide variety of aprotic, polar solvents may be used. Protic solvents and mixtures of polar aprotic and protic solvents, which have been shown to work well for the decarboxylation reaction alone, are not suited for the one-pot conversion of cinnamic acids to substituted GS due to reaction of the protic solvents with the halomethyloxirane. A single aprotic, polar solvent may be used. Additionally, mixtures of aprotic, polar solvents, and mixtures of aprotic, polar solvents with nonpolar solvents may be used. Suitable aprotic, polar solvents include, but are not limited to, N,N-dimethylformamide (DMF), 1-methyl-2-pyrrolidinone, N,N-dimethylacetamide (DMAc), dimethylsulfoxide, hexamethylphosphoramide, and hexamethylphosphorous triamide. Particularly useful in the present method are the solvents DMF and DMAc.

Polymerization Inhibitors

Polymerization inhibitors are useful but not required in the methods of the invention. Any suitable polymerization inhibitor that is tolerant of the temperatures required for the decarboxylation reaction as described in the invention may be used. Examples of suitable polymerization inhibitors include, but are not limited to, 4-methoxyphenol (MEHQ), hydroquinone, 4-tert-butyl catechol, phenothiazine, N-oxyl(nitroxide) inhibitors, including Prostab® 5415 (bis(1-oxyl-2,2,6,6-tetramethylpiperidine-4-yl)sebacate, CAS#2516-92-9, available from Ciba Specialty Chemicals, Tarrytown, N.Y.), 4-hydroxy-TEMPO (4-hydroxy-2,2,6,6-tetramethylpiperidin-1-yloxy, CAS#2226-96-2, available from TCI America) and Uvinul® 4040 P (1,6-hexamethylene-bis(N-formyl-N-(1-oxyl-2,2,6,6-tetramethylpiperidine-4-yl)amine, available from BASF Corp., Worcester, Mass.). A polymerization inhibitor may be included initially at the start of the reaction, added following decarboxylation, or added following synthesis of the glycidyloxystyrene monomer or substituted glycidyloxystyrene monomer.

Polymerization Retarders

In some instances it may be advantageous to use a polymerization retarder in the present reaction in combination with the polymerization inhibitor. Polymerization retarders are well known in the art and are compounds that slow down the polymerization reaction but cannot prevent it altogether. Common retarders are aromatic nitro compounds such as dinitro-ortho-cresol (DNOC) and dinitrobutylphenol (DNBP). Methods for the preparation of polymerization retarders are common and well known in the art (see for example U.S. Pat. No. 6,339,177; Park et al., Polymer (Korea) (1988), 12(8), 710-19) and their use in the control of styrene polymerization is well documented (see for example Bushby et al., Polymer (1998), 39(22), 5567-5571). A polymerization retarder may be included initially at the start of the reaction, added following decarboxylation, or added following synthesis of the glycidyloxystyrene monomer or substituted glycidyloxystyrene monomer.

Decarboxylation Conditions

The phenolic substrate, the non-amine basic catalyst, and the aprotic, polar solvent are added to a reaction vessel to form a reaction mixture. Any suitable reaction vessel may be used.

Reaction temperatures may vary depending on the concentration of substrate, type of substrate, the stability of the product formed, choice of catalyst and yield desired, which is readily determined by one skilled in the art. Typically, temperatures of at least about 100° C. are suitable where temperatures in the range of at least about 100° C. to about 200° C. are consistent with effective production of product. For the reaction using p-hydroxycinnamic acid as substrate, the preferred temperature range is from about 120° C. to about 150° C. For substrates that give a less stable product, e.g., caffeic acid, lower temperatures in the range of about 100° C. to about 120° C. are used. Higher temperatures in the range of about 150° C. to about 200° C. may be used with substrates that give a more stable product, e.g., 3,5-dimethyl-4-hydroxycinnamic acid.

The reaction may be carried out at a pressure ranging from atmospheric pressure to about 1000 psig (6895 kPa). A pressure of about 500 psig (3447 kPa) may be used. The pressure may be adjusted using an inert gas such as nitrogen. For reactions at elevated pressures, any conventional pressure reaction vessel may be used including, but not limited to shaker vessels, rocker vessels, and stirred autoclaves.

There is no limit on the time for the reaction; however, most reactions will run in less than six hours and reaction times of about 45 minutes to about 4.5 hours are typical for the production of the decarboxylated product of the phenolic substrate, which is the decarboxylated intermediate.

GS Synthesis Conditions

The decarboxylated intermediate resulting from the decarboxylation step is not isolated or prepared, but directly converted as shown for pGS synthesis from pHCA via a hydroxystyrene monomer (HSM) intermediate in Diagram I. The direct conversion without isolation, providing a one-pot two-step process, is advantageous due to instability of the intermediate to isolation.

Diagram I

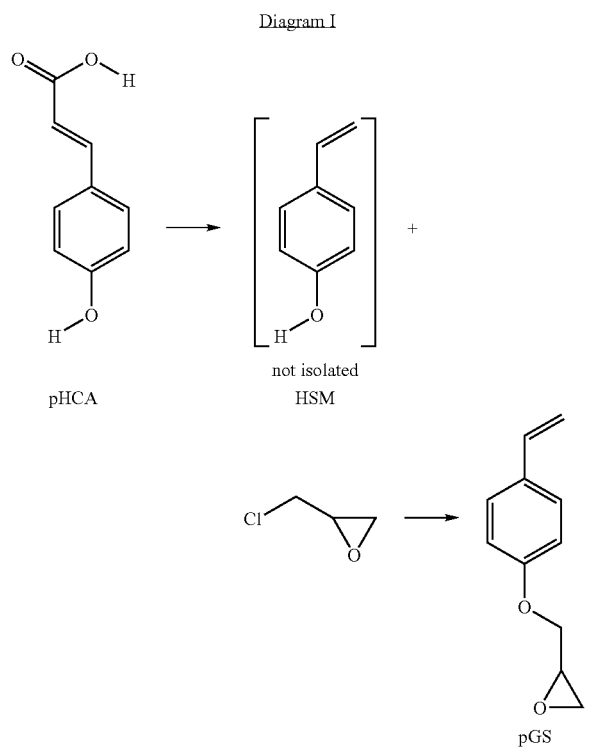

Synthesis of GS from a decarboxylated intermediate is initiated by addition of a halomethyl-oxirane and a base such as potassium hydroxide, potassium carbonate, or a tertiary amine. The base is typically added to a concentration that is between about 0.5 M and about 3.0 M. Examples of halomethyl-oxiranes that may be used in the reaction include epichlorohydrin, epibromohydrin (either enantiomer) and 2-(chloromethyl) 2-methyl oxirane. Particularly suitable is epichlorohydrin. The halomethyl-oxirane is used in low to moderate excess. Though halomethyl-oxirane may be used in higher amounts, for economical reasons it is particularly suitable to use halomethyl-oxirane at about 14 or less equivalents with respect to the amount of the decarboxylated intermediate; more specifically between about 2 and about 14 equivalents. Applicants have found that using the present method, these low to moderate excesses of halomethyl-oxirane, which are practical for commercial scale synthesis, are sufficient to obtain good yield of product while minimizing impurities resulting from attack of the phenolic group on the oxirane functionality. Particularly useful is between about 5 and about 7 equivalents of halomethyl-oxirane. Using these amounts in the present method, there is limited synthesis of the unwanted by-product that results from attack of GS by a second decarboxylated intermediate molecule, opening the oxirane ring and leading to a dimeric type product. The formation of this by-product may be further reduced in one embodiment of the present method, through contact of the decarboxylated phenolic substrate and the halomethyl-oxirane by adding the decarboxylated intermediate solution dropwise to the halomethyl-oxirane at about 90° C. to about 120° C.

Yields of GS product depend on the conditions of the reactions as exemplified in the Examples herein. Yields that are above 60% may be readily achieved.

The reaction mixture is brought to a temperature that is between about 20° C. and about 120° C. Particularly suitable is a temperature that is between about 80° C. and about 120° C., with 90° C. most preferred. The reaction mixture containing the decarboxylated intermediate may be cooled to between about room temperature (about 20-23° C.) and about 90° C. prior to addition of the halomethyl-oxirane and base catalyst to reduce potential exotherm upon addition of the halomethyl-oxirane. Alternatively, cooling may be omitted and the halomethyl-oxirane added slowly, however this leads to greater formation of the unwanted dimeric product.

The reaction is run for a period of about 30 minutes to about 8 hours, with about 80 minutes being particularly suitable. The pressure may be as described in the decarboxylation reaction.

Isolation and Purification of GS Product

After completion of the reaction, the GS product may be isolated using any suitable method known in the art including filtration and/or extraction. If not present in the reaction, a polymerization retarder or inhibitor may be added prior to isolation. Isolation may include, for example, cooling the reaction mixture to room temperature and filtering to recover solids. The solids may be extracted with organic solvents, the extracts may then be concentrated and vacuum distilled. Alternatively, the reaction mixture may be poured onto ice water and extracted into an organic solvent, such as ethyl acetate or diethylether. Then the product may be recovered by removing the solvent using evaporation at reduced pressure. The product may be further purified using recrystallization, vacuum distillation, flash distillation, or chromatographic techniques that are well known in the art. The yield of the GS product is at least about 48% of the theoretical yield. Under more optimal conditions as provided in Example 2 Table 1, yield is 68% of the theoretical yield or greater.

The resultant GS product may then be used as monomers for the production of resins, elastomers, adhesives, coatings, automotive finishes, inks, and as additives in elastomer and resin formulations. In some applications, isolation of the GS monomer is not necessary.

GS Polymerization

GS synthesized as described above may be used to form homopolymers or copolymers. The GS may be purified or used without purification. Preferably the GS is purified as described herein above prior to polymerization.

As is well known in the polymerization art, varying the concentration of the monomer prior to performing the polymerization reaction affects the molecular weight of the polymer obtained. Thus the concentration of GS, and additional monomer if using copolymerization, may be varied depending on the desired molecular weight of the polymer or copolymer to be made. In addition, the molecular weight may be controlled by the solvent used, amount of initiator added, addition of chain transfer agents, use of living polymerization techniques, and temperature of the reaction.

Optional Co-monomers

One or more monomers may be added to the GS product to produce a copolymer. Additional monomers are known in the art and include, without limitation, (1) styrene and substituted styrenes such as divinylbenzene, 4-methylstyrene, pentafluorostyrene, styrene alkoxide wherein the alkyl portion is $C_1$-$C_5$ straight or branched chain and the like; (2) acrylates such as methyl acrylate, ethyl acrylate, lauryl acrylate, 2-hydroxyethyl acrylate, t-butyl acrylate, MAA—methyl adamantyl acrylate, ETCDA—ethyl tricyclodecanyl acrylate, cyclohexylacrylate and the like; (3) methacrylates and dimethacrylates such as methyl methacrylate, lauryl methacrylate, stearyl methacrylate, 2-ethylhexyl methacrylate, MAMA— methyl adamantyl methacrylate, EAA—ethyl adamantyl acrylate, EAMA—ethyl adamantyl methacrylate, ETCDMA—ethyl tricyclodecanyl methacrylate, PAMA—propyl adamantyl methacrylate, MBAMA—methoxybutyl adamantyl methacrylate, MBAA—methoxylbutyl adamantyl acrylate, isobornylacrylate, isobornylmethacrylate, cyclohexylmethacrylate and the like; (4) polymerizable fluorine-containing compounds such as fluoroalkylsubstituted acrylates and methacrylates including compounds sold by DuPont under the ZONYL® name with general structure $CH_2$=$CHCO_2CH_2CH_2(CF_2)_nCF_3$ and $CH_2$=$C(CH_3)CO_2CH_2CH_2(CF_2)_nCF_3$, and the like; and (5) other co-monomers such as acrylic acid, methacrylic acid, maleic acid, fumaric acid, maleic anhydride, acrylonitrile, acrylamides, methacrylamides, and the like.

Particularly useful are copolymers of GS with HSM and of GS with styrene. Typically one type of GS and one type of HSM are copolymerized, although multiple types of each may be used. GS copolymers with HSM may be prepared by copolymerizing acetoxystyrene monomers and GS followed by removal of acetoxy groups as is well known in the art. Alternatively, GS may be directly copolymerized with HSM following a method disclosed in U.S. Pat. No. 6,864,324, which is herein incorporated by reference. In this method, HSM is directly copolymerized with a comonomer in a reaction containing a polar organic solvent and a polymerization initiator, that is incubated at a temperature and time sufficient to produce a poly(hydroxystyrene).

The general structures of these copolymers are shown in Diagrams II and III, respectively.

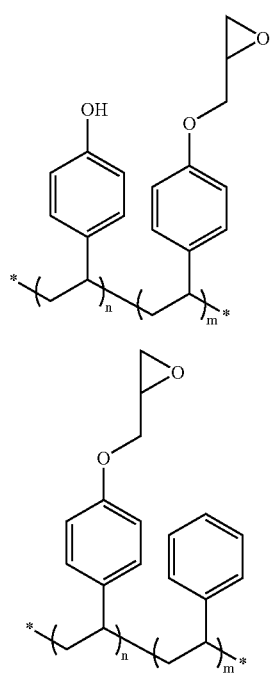

Diagram II

Diagram III where n and m each may vary independently between each successive set of monomers creating random copolymers of molecular weights between about 2,000 and about 1,000,000.

Polymerization Initiators

Polymerization GS may be by cationic polymerization of the vinyl group with an $HI/I_2$ initiating system, as shown for both alpha methyl styrene and styrene containing the para glycidyloxy group, described by Hashimoto (J. Polym. Sci. Polym. Chem. Ed. 25:1073 (1987)). Typically HI is first added to a dry solution of the monomer in methylene chloride at a temperature between about −15° C. to −40° C. Iodine is then added at the same temperature. After the polymerization is complete, the reaction is quenched by addition of ammoniacal methanol and washed with water and sodium thiosulfate solutions. In addition, living cationic polymerization may be used at lower temperatures (about −78° C.) where the $HI/I_2$ or $I_2$ initiated polymerization species are long lived, behaving like living systems (Hashimoto, supra).

Polymerization may use any free radical initiator that achieves the desired end result. The initiator may be selected from the group consisting of 2,2'-azobis(2,4-dimethylpentanenitrile) known as Vazo® 52, 2,2'-azobis(2-methylpropanenitrile), 2,2'-azobis(2-methylbutanenitrile) known as Vazo® 67, 1,1'-azobis(cyclohexanecarbonitrile) known as Vazo® 88, azobis(isobutyrylnitrile) known as Vazo® 64, t-butyl peroxy-2-ethylhexanoate, t-butyl peroxypivalate, t-amyl peroxypivalate, diisononanoyl peroxide, decanoyl peroxide, succinic acid peroxide, di(n-propyl)peroxydicarbonate, di(sec-butyl)peroxydicarbonate, di(2-ethylhexyl) peroxydicarbonate, t-butylperoxyneodecanoate, 2,5-dimethyl-2,5-di(2-ethylhexanoylperoxy)hexane, t-amylperoxyneodecanoate, dimethyl 2,2'-azobisisobutyrate and combinations thereof. Particularly suitable is Vazo® 64.

The amount of initiator is any amount that accomplishes the desired end result and is selected based upon factors including concentration of monomer, identity and amount of co-monomer(s), temperature, solvent and desired molecular weight.

Chain transfer agents known to one skilled in the art may be used in the present method. Commonly used chain transfer agents are alkylthiols. Particularly suitable is 1-dodecanethiol. Alternatively, as taught in US Patent Publication Nos. 2004-171777 and US2004-024132, chain transfer agents such as thiocarbonylthio compounds may be used in the polymerization reaction in a process called Reversible Addition Fragmentation (RAFT) polymerization. In this case a RAFT reagent may be used as is well known to one skilled in the art. The synthesis of trithiocarbonate type RAFT reagents and their use are described in WO 99/31144 and EP 1479700, which are herein incorporated by reference.

Alternatively, the glycidyloxy group of the monomer may be polymerized. It can be used to derivatize alcohol and amine containing substrates to give materials which are radically polymerizable; see for example WO9731026 which describes forming gels from polyhydroxy polymers substituted with styryl ether groups. For example, the glycidyloxy group can be made into polyether by reaction with diols, or into polyamines by reaction with diamines. These types of polymerizations leave the vinyl group free for other reactions such as cross linking.

Polymerization Reaction Conditions

The polymerization conditions are any temperature and pressure that will produce the desired end result. In general, the temperatures are from about 30° C. to about 100° C., preferably from about 40° C. to about 100° C., and most preferably from about 45° C. to about 90° C. The pressure may be atmospheric, sub-atmospheric or super-atmospheric. The polymerization time is not critical, but generally will take place over a period of at least one minute to about 24 hours in order to produce a polymer of desired molecular weight.

All reagents, including the initiator, optional co-monomer(s) and optional additional solvent(s) may be added to the GS product monomer and solvent mixture in the reactor prior to commencing the polymerization reaction, or alternatively may be fed to the reactor as the reaction proceeds, such as metered feed of one or more co-monomers to achieve higher compositional uniformity, or alternatively or additionally adding additional initiator to achieve higher conversion of all monomer(s).

Conducting the polymerization reaction in a reactor fitted with a reflux condenser provides the benefit of additional heat transfer area to remove the polymerization exotherm. The solvent and the operating pressure may be selected so that the boiling point of the polymerization reaction mixture is the desired temperature. Solvents useful for polymerization of styrenes, which are well known in the art, can be used. Pressure may be changed as desired over the course of the polymerization. An additional solvent, or mixture thereof, may be added to affect boiling point or other aspects of the polymerization. When the GS is not purified prior to polymerization, a solvent such as DMAc or DMF is preferred.

Resulting Polymers

Using the present method of synthesis of GS, together with the polymerization described herein, polymers that are completely functionalized may be prepared on a commercial scale. In particular, completely functionalized polymers of GS that range in weight average molecular weight up to about 1,000,000 may be prepared. Polymers of about 6 to about 10,000 are particularly useful in preparing coatings. The complete functionality is provided by the instant method, due to complete glycidyloxilation occurring prior to polymerization. In commercial processes known in the art, for example in U.S. Pat. No. 6,391,979, glycidyloxilation occurs following polymerization, in which case glycidyloxilation is typically incomplete, resulting in impure polymers including non-glycidyloxilated positions. The completely functionalized polymer of GS has the structure shown in Diagram IV.

Diagram IV

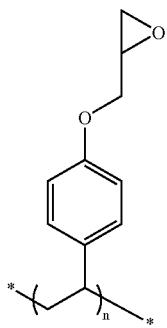

where n is between about 10 and about 6000.

Optional Purification of Homopolymers and Copolymers of GS Product

Polymers produced in the present method may be purified by cooling the reaction mixture to room temperature and adding it dropwise to a non-solvent, typically a hexane such as petroleum ether or toluene, with stirring, forming a precipitate. The precipitate is then collected and washed. These steps may be repeated by redissolving the precipitate in a solvent and again adding the resulting solution to a nonsolvent, then collecting the precipitate to further purify.

Alternatively, after the polymerization reaction the polymer may be subjected to a purification procedure such as that described in U.S. Pat. No. 6,864,324 wherein the same type organic solvent used in the reaction (first solvent) is used to purify the polymer via a multi-step fractionation process. Additional first solvent is added to the polymer mixture, and the resultant slurry is stirred vigorously and/or heated to boiling for several minutes, and then chilled to as low as 25° C. and allowed to stand. This permits the slurry to produce a phase separation, and then the liquid is removed by centrifugation, filtration, decantation or by similar means. The process is repeated at least one more time until no further purification is identified, as for example, until a small sample of the decanted solvent, upon evaporation to dryness, shows substantially no residue. This fractionation process is generally carried out 2 to 10 times, i.e. heating, cooling, separating, and the solvent replacement.

One of the important measures of the degree of impurity of the crude polymer produced from the polymerization of the monomers is the polydispersity value. In general, it is desirable to have a low value, for example, less than about 3; the lower value is indicative that the polymerization reaction was more uniform in chain length. The uniqueness of this purification step is that the desired polymer formed is, to some degree, not soluble in the solvent and that the undesired, low molecular weight average polymers and undesired monomers are soluble in the solvent. Thus the purification/fractionalization provides the removal of these undesirable materials. In general, the polydispersity of the crude polymer is measured before, during and after this purification/fractionalization step, with the objective of reducing this value by at least about 10% of what the value of the original crude polymer was before the purification treatment. Preferably, it is desirable to yield a product whose polydispersity is below about 2.0. It is to be understood that polydispersity means the ratio of weight average molecular weight (Mw) over the number average molecular weight (Mn) as determined by Gel Permeation Chromatography (GPC).

Another optional purification utilizes a second solvent which is immiscible with the solvent utilized for the polymerization reaction. The second solvent is added to the poly(GS) mixture until a second layer is formed. The mixture is then stirred vigorously or is heated to boiling for several minutes and then allowed to stand until cool. A discrete second layer is formed which is then removed by decantation or similar means, and the process is repeated until no further purification is identified, as for example, until a small sample of the decanted solvent upon evaporation to dryness shows no residue. In this fashion, by-products and low weight average molecular weight materials are removed.

The polymer solution is then subjected to distillation to remove the remaining second solvent. Most often removal of the second solvent is accomplished by azeotropic distillation, with the azeotropic mixture boiling below the boiling temperature of either the first or the second solvent.

Typical second solvents useful for the method of this step include hexane, heptane, octane, petroleum ether, ligroin, lower alkyl halohydrocarbons, i.e., methylene chloride, and the like.

Applications

Polymers and copolymers of GS may be used in many applications. Due to the large number of reactive groups in these polymers, highly crosslinked materials result upon curing. The high density of crosslinking in these epoxy materials provides for high chemical and heat resistance. Therefore, these polymers and copolymers can be used in applications where properties of chemical and thermal resistance are desired such as in various resins and protective coatings. For example, protective coatings may be used in oil refineries, petrochemical plants, marine applications, and for vessels that transport or store chemicals, such as tankers and train cars, as well as in pipes, tanks, drums and other containers. Vessel or other coatings may be referred to as claddings.

Compositions containing polymers or copolymers made using the present method may be prepared by methods well known to one skilled in the art. Crosslinking may be accomplished by reacting with tertiary, secondary, or primary amines, anhydrides, acids, Lewis acids, Lewis bases, amides, imidazoles, ureas, melamines, cyanate esters, or other commonly used curing agents and catalysts. Curing may be heat-curing or room temperature curing.

In addition to the polymers or copolymers, compositions may include solvents, diluents, plasticizers, accelerators, curatives, tougheners, fillers, pigments, flow control agents, or other modifiers. Typical hardeners, as well as acrylics or polyesters may be included.

The viscosity of compositions containing polymers and copolymers of GS may be altered by heating and/or by adding a diluent such as a low molecular weight epoxide of a dihydric phenol (such as resorcinol), toluene, or xylene. Lowering viscosity may be desired prior to application, such as for applying the composition as a coating on a surface.

Application may be by brushing, spraying, dipping, using a roller, electrodeposition, or other typical methods. Alternatively, the present compositions may be cast or molded, such as using compression molding.

Compositions containing polymers or copolymers made using the present method may also be used as structural composites. Such composites may include glass, graphite, boron, carbon, or Kevlar fibers.

In addition, compositions containing polymers or copolymers made using the present method may be used in any application of epoxy resins, such as described in U.S. Pat. No. 6,391,979, which is herein incorporated by reference.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "sec" means second(s), "mL" means milliliter(s), "L" means liter(s), "μL" means microliter(s), "μm" means micrometer(s), "mol" means mole(s), "mmol" means millimole(s), "g" means gram(s), "mg" means milligram(s), "ppm" means parts per million, "M" means molar concentration, "m" means molal concentration, "eq" means equivalents, "v/v" means volume to volume ratio, "Pa" means pascal, "mPa" means millipascal, "psig" means pounds per square inch gauge, "MHz" means megahertz, "TLC" means thin layer chromatography, "HPLC" means high performance liquid chromatography, "LC-MS" means liquid chromatography-mass spectrometry, "NMR" means nuclear magnetic resonance spectrometry, "DMF" means N,N-dimethylformamide, "DMAc" means N,N-dimethylacetamide, "NMP" means 1-methyl-2-pyrrolidinone, "nd" means not determined, "kPa" means kilopascal(s), "rpm" means revolutions per minute, and "UV" means ultraviolet, "RT" means room temperature, "THF" is tetrahydrofuran "MEHQ" means 4-methoxyphenol, "Mn" means number average molecular weight, "Mw" means weight average molecular weight, "Mz" means weight squared average of molecular weight.

Reagents:

Para-hydroxycinnamic acid was obtained from Aldrich (Milwaukee, Wis.) or TCI America (Portland, Oreg.), unless otherwise noted. All solvents were reagent grade and were obtained from Aldrich. The polymerization inhibitor Prostab® 5415 was obtained from Ciba Specialty Chemicals, Tarrytown, N.Y.

Analytical Methods

HPLC Methods:

The Agilent 1100 HPLC system was used with a reverse-phase Zorbax SB-C18 column (4.6 mm×150 mm, 3.5 μm, supplied by Agilent Technologies). The HPLC separation was achieved using a gradient combining two solvents: Solvent A, 0.1% trifluoroacetic acid in HPLC grade water and Solvent B, 0.1% trifluoroacetic acid in acetonitrile. The mobile phase flow rate was 1.0 mL/min. The solvent gradient used is given in Table 1. A temperature of 40° C. and a sample injection of 1 μL were used.

TABLE 1

Solvent Gradient Used for HPLC

| Time (min) | Solvent A | Solvent B |
|---|---|---|
| 0 | 95% | 5% |
| 10 | 100% | 0% |
| 12 | 100% | 0% |
| 12.5 | 95% | 5% |

Suitable calibration curves were generated using standard pHS, pHCA and pGS solutions. The pHS for the standards was prepared using a method similar to that described by Leuteritz et al. (*Polymer Preprints* 43(2):283-284 (2002)). The calibration curves were used to determine wt % of pHCA and pHS in each sample from HPLC peak areas. With this information and the total weight of the reaction mixture at the time of sampling, the % conversion of pHCA and the % yield of pHS and pGS were calculated.

$^1$H NMR:

The proton NMR data was obtained using a Bruker DRX (Bruker NMR, Billerica, Mass.) at 500 MHz.

LC-MS Method:

A Hewlett Packard LC/MSD Series 1100 instrument (Agilent Technologies, Wilmington, Del.) was used for the LC-MS analysis. A Zorbax Eclipse XDB-C18 column (2.1 mm×50 mm, MAC-MOD Analytical Inc.) was used in the LC separation with a solvent gradient consisting of two solvents, solvent A, 0.05% trifluoroacetic in water and solvent B, 0.05% trifluoroacetic acid in acetonitrile. The gradient was from 95% solvent A to 0% solvent A over 4.5 min, followed by 2.5 min with 0% solvent A and then returned to 95% solvent A, with a flow rate of 0.8 mL/min. The LC separation was done at a temperature of 60° C. with detection at 220 nm.

GC Method:

An HP Gas Chromatograph 5890 Series II (Hewlett-Packard Co., Palo Alto, Calif.) was used with a J&W Scientific, DB-1 (30 m×0.25 mm×0.25 μm) column, a cup-type packed injection liner, and a flame ionization detector. The column flow rate of helium gas was 1.2 mL/min. Inlet temperature was 200° and detector temperature was 285°. Injection volume was 1 μl. The GC separation was achieved with the following temperature program with a 20 min. total run time: initial temperature of 60° for 1 minute; increasing 20°/minute to a final temperature of 280°, and holding at that temperature for 8 minutes.

An injection of solvent was made prior to sample injection. Both a standard and samples were diluted in DMF prior to injection to provide suitable peak intensity. The syringe was washed with solvent multiple times before and after injection.

GC/MS

GC/MS was performed on an HP-6890 GC instrument equipped with an HP-5973 mass selective detector (MSD) and autosampler. A DB-5MS column (J&W Scientific) that was 30 m length×0.25 mm ID×0.25 μm film thickness was used. The profile included an initial temperature of 70° C. held for 4 min, then increases of 10° C./min to 300° C. and held for 7 min. Injection was of 1 μl.

GPC:

GPC was performed on a Waters gel permeation chromatograph equipped with a refractive index detector.

Example 1

One-Pot Process for Making p-Glycidyloxystyrene from the Decarboxylation of pHCA Followed by Reaction of 4-Hydroxystyrene (HSM) with Epichlorohydrin The purpose of this example was to demonstrate the synthesis of p-glycidyloxystyrene in a one-pot, two step process from p-hydroxycinnamic acid. p-Hydroxycinnamic acid (180.596 g, 1.100 mol) and 562.8 g of N,N-dimethylacetamide (DMAc, reagent grade) were charged into a 1-L, 4-neck round-bottom flask equipped with a reflux condenser, magnetic stirring, internal thermowell and thermocouple, septum inlet adapter, and nitrogen. The mixture was stirred at room temperature for 10 min. Separately, an oil bath was preheated to 153° C., and then raised in position to heat the reaction flask, which was allowed to equilibrate at 150° C. Then, 1.508 g of potassium acetate (1.4 mol %) was weighed in a drybox and added to the reaction mixture in one portion. The reaction was heated for 210 min at 150° C. After this time, a sample of the reaction mixture was removed for HPLC analysis as described in General Methods. The HPLC results indicated the presence of 0.006 mol of pHCA and 1.181 mol HSM. These values are consistent with an essentially quantitative conversion of pHCA to HSM. The oil bath was lowered from the flask, and the oil bath and flask were allowed to cool to room temperature. The reflux condenser was replaced with a short path distillation head. The oil bath was adjusted to 40° C. and was raised again to the flask. Under reduced pressure of approximately 250 millitorr (33 Pa), 282.62 g of DMAc was collected, leaving approximately 413 g of solution. A sample of the solution was analyzed using HPLC and found to have an HSM concentration of 34.46 wt %. A portion of the HSM solution was used in the next step.

In the drybox, KOH was pulverized with a mortar and pestle. The finely ground KOH (1.102 g, 16.7 mmoles, 1.1 eq) was charged into a 25 mL round-bottom flask, the flask was sealed, and then removed from the drybox. HSM solution (5.279 g, ~15.14 mmoles, 1 eq) was charged to the round-bottom flask. Epichlorohydrin (20.707 g, 0.224 moles, 14.8 eq) was charged to the round-bottom flask. The flask was equipped with a reflux condenser, magnetic spinbar, and nitrogen. The flask was lowered into a preheated oil bath at 90° C. The reaction solution became thick with solids as it heated to 90° C. The reaction mixture was heated for 1 h. After 1 h, the round-bottom flask was removed from the oil bath. A GC chromatogram (HP 5890 Series II) showed reaction completion (no HSM present). The reaction mixture was filtered through a glass-fritted, medium porosity filter and washed with minimal DMAc. The resulting reaction solution was concentrated on a rotary evaporator with heat (60° C.) under reduced pressure (high vacuum; to 300 millitorr). A slightly turbid, yellow oil was produced with wt.=2.404 g. The oil was stored in a refrigerator at 0° C. The oil solidified in the refrigerator.

The solid was removed from the refrigerator and allowed to thaw. Then 25 mL diethyl ether was added to the oil. The solution was filtered through a Celite® pad and rinsed with additional diethyl ether (a residue remained on the inside walls of the flask; ~0.041 g in wt.). The diethyl ether solution was concentrated on the rotary evaporator and dried further on a high vacuum line. A clear yellow oil was obtained with wt.=2.112 g.

A high vacuum distillation was performed. Prior to the distillation, ~1 mg MEHQ (hydroquinone monomethylether) was added to the crude monomer. Two fractions were collected as listed in Table 2.

TABLE 2

Fractions of monomer collected from distillation.

| Fraction | Temperature (° C.) | Pressure (milliTorr) | Wt. (grams) | Description |
| --- | --- | --- | --- | --- |
| 1 | 69-71 | 80 | 0.124 | frozen; thawed to clear oil |
| 2 | 75-80 | 80 | 1.436 | frozen; thawed to clear oil |

~500-1000 ppm MEHQ was added to each fraction. The fractions were stored at 0° C. $^1$H NMR (CDCl$_3$) for each fraction was consistent with p-glycidyloxystyrene. GC/MS was consistent with p-glycidyloxystyrene (m/z=176). The isolated yield, after purification, was 58.5% based upon starting HSM.

Example 2

One Pot Process for Making p-Glycidyloxystyrene from pHCA via p-Hydroxystyrene as Intermediate Using Low Amount of Epichlorohydrin Into a three neck 1 Liter flask equipped with a mechanical overhead stirrer and water condenser under an atmosphere of Nitrogen, was added 100 g (0.609 Mole) of p-hydroxycinnamic acid (TCI America; Portland, Oreg.) followed by 316 ml of N,N-Dimethylacetamide. The solution was stirred to form a light tan solution. To the solution was added 2.98 g of potassium acetate (Aldrich; Milwaukee, Wis.) (5 Mole %) followed by 0.1 g of 4-methoxyphenol (200 ppm; Aldrich; Milwaukee, Wis.). The flask was lowered into an oil bath preheated to 150° C. The reaction progress was monitored by HPLC as described in General Methods. The reaction mixture turned dark brown in color. Complete decarboxylation of p-hydroxycinnamic acid occurred in 4.5 h to give a solution of p-hydroxystyrene (HSM). The flask was then removed from the oil bath and allowed to cool to 40° C. To the reaction mixture was added 34.2 g finely ground potassium hydroxide, followed by rapid addition of 333.6 mL (7 equivalents) of epichlorohydrin (Aldrich). The reaction mixture turned yellow. The flask was lowered into a 90° C. oil bath. Reaction progress was monitored by HPLC. The p-hydroxystyrene was completely consumed in 80 min. with formation of p-glycidyloxystyrene, 68.07% yield based on HPLC. The reaction mixture was cooled to room temperature then filtered through a medium sintered funnel. The solids were washed with a small portion of DMAc and then with diethylether. Prostab® 5415 (1000 ppm; (bis(1-oxyl-2,2,6,6-tetramethylpiperidine-4-yl)sebacate; Ciba Specialty Chemicals, Tarrytown, N.Y.) was added and the mixture concentrated via rotovap at 40° C. The product was purified by vacuum distillation. The product fractions were collected at 98-100° C. and $2.2 \times 10^{-2}$ Torr. Fractions were analyzed by $^1$H NMR in CDCl3 as described in General Methods. The fractions with good product were combined to produce total of 64.2 g of clear liquid.

Example 3

One Pot Preparation of p-Glycidyloxystyrene from pHCA via p-Hydroxystyrene as Intermediate with Varying Reaction Conditions Preparation of pGS was as described in Example 2, with variations in reaction components including the base used (amount and/or type), and the temperature at which the addition of epichlorohydrin occurred. The reaction components and conditions are given for each reaction (rxn), as well as the yields, in Table 3. All reactions were run for 90 min. The KOAc is added in the first step to catalyze the decarboxylation of pHCA to HSM. Either $K_2CO_3$ or KOH was then added to facilitate the second step of the reaction sequence. The decarboxylation was run at 150° C., then the temperature was reduced to that given in Table 3 and epichlorohydrin was added and the second reaction performed.

Example 4

One Pot Preparation of p-Glycidyloxystyrene from pHCA via p-Hydroxystyrene with Inverse Order of Addition of Epichlorohydrin A solution of pHS was prepared and assayed as described in Example 1 above using 5 g of pHCA and 0.149 g of KOAC catalyst. The solution was allowed to cool to room temperature at which time 1.71 g of freshly ground KOH was added. In a separate 50 mL flask was added 5.63 g epichlorohydrin. The contents of the first flask were added dropwise to the epichlorohydrin at either 25° C., 90° C., or 100° C. (See Table 3). When addition was complete, the flask was brought to 90° C. or maintained at 90° C. or 100° C., and the reaction run for 90 min. Progress was monitored by HPLC. Yields were calculated based on HPLC as described in the General Methods above. Yields are given in Table 4.

TABLE 4

Effects of inverse order additions and epichlorohydrin variations on yields of pGS.

| Rxn | pHCA (gm) | KOAc (gm) | KOH (gm) | Epichlorohydrin (gm) | Equiv. Epichlorihydrin | Temp of Addition ° C. | PGS (% yield) |
|---|---|---|---|---|---|---|---|
| 8 | 5 | 0.149 | 1.71 | 5.6367 | 2 | 25 | 59.48 |
| 9 | 5 | 0.149 | 1.71 | 5.6367 | 2 | 90 | 49.9 |
| 10 | 5 | 0.149 | 1.71 | 11.2731 | 4 | 100 | 69.7 |
| 11 | 5 | 0.149 | 1.71 | 11.2731 | 4 | 100 | 65.15 |

Example 5

Preparation of 2-(2-Methoxy-4-vinyl-phenoxymethyl)-oxirane

Into a 100 mL 3 neck flask was added 10 g trans-3-methoxy-4-hydroxycinnamic acid (ferulic acid; Aldrich), 10 mg MEHQ and 29 mL DMAc. To the resulting solution was added 0.257 g KOAc and the mixture heated to 120° C. The reaction was monitored using the HPLC method described in General Methods. The reaction was complete in 135 min. The flask was removed from the oil bath and allowed to cool to 40° C. To reaction mixture was added 2.89 g (0.0515 M) powdered potassium hydroxide followed by rapid addition of 33.35 g (0.36 M) of epichlorohydrin. The reaction mixture was heated to 90° C. for 1 hr 15 min, at which point all of the intermediate 3-Methoxy-4-hydroxystyrene was consumed

TABLE 3

Effects of reaction component variations on yields of pGS.

| Rxn | pHCA (gm) | KOAc (gm) | $K_2CO_3$ (gm) | KOH (gm) | Epichlorohydrin (gm) | Molar Equiv. Epichlorohydrin | Temp. of addition ° C. | PGS (% yield) |
|---|---|---|---|---|---|---|---|---|
| 1 | 20 | 0.168 | 18.5 | 0 | 22.58 | 2 | 90 | 29 |
| 2 | 20 | 0.168 | 0 | 8.7 | 22.58 | 2 | 90 | 55 |
| 3 | 2 | 0.017 | 0 | 0.752 | 5.694 | 5 | 40 | 71 |
| 4 | 50 | 1.49 | 0 | 17.1 | 197.3 | 7 | 90 | 72 |
| 5 | 50 | 1.49 | 0 | 17.1 | 197.3 | 7 | 40 | 48 |
| 6 | 50 | 1.49 | 0 | 17.1 | 197.3 | 7 | 90 | 66 |
| 7 | 100 | 2.98 | 0 | 34.2 | 394.6 | 7 | 40 | 68 |

(determined by HPLC analysis) and converted to desired Product A: 2-(2-Methoxy-4-vinyl-phenoxymethyl)-oxirane.

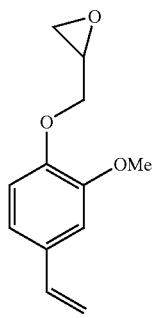

Product A

The reaction mixture was cooled to RT, filtered using filter paper to remove salt, and washed twice with small amount of DMAc. The filtrate was transferred to a one neck flask and solvent was removed on rotovap at 45° C. using high vacuum. The residual liquid (17 g) was transferred to a 35 ml flask and distilled, with the product coming over at 108-110° C. (distilling head temp) and pressure $8.3 \times 10^{-3}$ torr. Collection was of 4.85 g of thick oil which solidified to a white solid in the collection flask. $^1$H NMR (CD$_2$Cl$_2$) δ=6.9d (J=1.9) 1H; 6.83 dd (J-8.2, 1.9) 1H; 6.75 d (J=8.2)1H; 6.56 dd (J=17.5, 10.9) 1H; 5.53 d (J=17.5) 1H; 5.06 d (J=10.9) 1H; 4.16 dd (J=11.2, 3.1) 1h; 3.8 m 2H; 3.77 s 3H; 3.23 m 1H; 2.75 t (J=4.8) 1H; 2.60 dd (J=4.8, 2.6) 1H. C$^{13}$ NMR (CD$_2$Cl$_2$): δ 150.5, 148.93, 137.2, 132.5, 120.05, 114.67, 112.85, 110.23, 70.97, 56.61, 50.82, 45.18

Example 6

Polymerization of p-Glycidyloxystyrene p-glycidyloxystyrene was polymerized using different reaction conditions as listed in Table 5. Either 1.76 g or 2 g of p-glycidyloxystyrene (prepared and purified as described in Example 1) was added to a 25 ml Schlenk tube. Between 2 ml and 9 ml of solvent (either dry THF or toluene) was added to each sample. To some samples was added either the chain transfer agent 1-dodecanethiol (Aldrich), or RAFT agent S-cyanomethyl S-dodecyl trithiocarbonate, in the amounts listed in Table 5. All samples received an azo initiator, either Vazo® 64 (azobis(isobutyrylnitrile); AIBN) or Vazo® 88 (1,1'-azobis(cyclohexanecarbonitrile); Aldrich).

The S-cyanomethyl, S-dodecyl trithiocarbonate was prepared as described in co-owned and co-pending U.S. patent application Ser. No. 11/289108 as follows. A 1000 mL 3-neck round bottom flask (fitted with mechanical stirrer, septum, thermocouple well, and reflux condenser with N$_2$ bubbler) was charged with sodium hydroxide (12.18 g, 304.5 mmol) and water (30 mL). Isopropanol (500 mL) was added to the solution of sodium hydroxide, and the reaction mixture was cooled to about 5° C. The cooled reaction mixture was treated dropwise with dodecanethiol (60.6 g, 300 mmol).

The reaction mixture was stirred for 30 min at 5° C., cooled to 0° C., and treated with carbon disulfide (24.0 g, 315 mmol) by syringe over a ca. 10 min period to produce a yellow solution which was stirred at ca. 0°-5° C. for 0.5 h. The reaction mixture was treated with chloroacetonitrile (23.8 g, 315 mmol) dropwise by syringe over a ca. 20 min period while maintaining the temperature between 0 and 5° C. The reaction mixture was stirred at 0° C. for 2 h.

The reaction mixture was warmed to ca. 30° C. and filtered to remove sodium chloride. The solid residue was washed with a 5 mL portion of isopropanol. The combined filtrate was treated with water (50 mL). Product crystals of S-cyanomethyl S-dodecyl trithiocarbonate were formed as the temperature decreased. After the bulk of crystals had formed at room temperature, the mixture was cooled to 0° C. for 1.5 h and the first crop of crystals was collected. There was obtained 82.3 g of bright yellow flakes after drying. The filtrate was treated with another 50 mL water and chilled to provide 8.5 g of the product in the second crop of crystals. $^1$H NMR analyses showed both crops of ca. 98% purity (93% isolated yield).

TABLE 5

Variables used in polymerization reactions of pGS.

| Rxn | Amt pGS (g) | Vazo 64 (mg) | Vazo 88 (mg) | THF (ml) | Tol (ml) | Temp (° C.) | Rxn Time (h) | Yield (%) | CTA (mg) | RAFT agent (mg) |
|---|---|---|---|---|---|---|---|---|---|---|
| 1 | 2 | 93.2 | 0 | 9 | 0 | 60 | 3 | 18.9 | 0 | 0 |
| 2 | 2 | 9.32 | 0 | 9 | 0 | 60 | 3 | 7.75 | 0 | 0 |
| 3 | 2 | 9.32 | 0 | 3.68 | 0 | 60 | 3 | 38.5 | 0 | 0 |
| 4 | 2 | 18.64 | 0 | 9 | 0 | 60 | 3 | 5.25 | 0 | 0 |
| 5 | 2 | 9.32 | 0 | 0 | 9 | 60 | 3 | 5.9 | 0 | 0 |
| 6 | 2 | 0 | 138.5 | 9 | 0 | 60 | 3 | 3.75 | 0 | 0 |
| 7 | 2 | 9.32 | 0 | 9 | 0 | 60 | 24 | 9.5 | 0 | 0 |
| 8 | 2 | 9.32 | 0 | 2 | 0 | 60 | 16 | 54.4 | 0 | 0 |
| 9 | 2 | 9.32 | 0 | 3.7 | 0 | 60 | 18 | 52.5 | 0 | 0 |
| 10 | 2 | 9.32 | 0 | 3 | 0 | 60 | 18 | 90.5 | 0 | 0 |
| 11 | 2 | 9.32 | 0 | 0 | 2 | 60 | 16 | 100 | 0 | 0 |
| 12 | 2 | 9.32 | 0 | 0 | 3 | 60 | 18 | 69 | 0 | 0 |
| 13 | 2 | 9.32 | 0 | 3 | 0 | 60 | 18 | 53 | 0 | 0 |
| 14 | 2 | 9.32 | 0 | 3 | 0 | 60 | 18 | 58.5 | 6.24 | 0 |
| 15 | 2 | 9.32 | 0 | 3 | 0 | 60 | 18 | 100 | 12.47 | 0 |
| 16 | 1.76 | 19.2 | 0 | 3.2 | 0 | 68 | 18 | 78.4 | 0 | 55.7 |
| 17 | 1.76 | 19.2 | 0 | 3.15 | 0 | 68 | 16 | 93.2 | 0 | 55.7 |

Rxn is reaction;
Tol is toluene,
CTA is the chain transfer agent 1-dodecanethiol.

Each tube was sealed with a rubber septum and then degassed by 3 cycles of freeze thaw pumping. Finally each tube was evacuated and the resulting reaction mixture was heated to 60° C. for the amount of time specified in Table 5. After cooling to room temperature, the reaction mixture was added drop wise to 20 ml petroleum ether in a beaker with vigorous stirring, which gave a white flocculent preipitate. The precipitate was collected on a medium sintered funnel and washed with cold petroleum ether to give the desired polymer. Polymer molecular weight was determined by GPC as described in General Methods and the results are given in Table 6.

TABLE 6

Molecular weights of pGS polymers produced from Table 5 reactions.

| Rxn | Mn | Mw | Mz | Polydispersity |
|---|---|---|---|---|
| 1 | 7954 | 16312 | 36108 | 2.051 |
| 2 | 21715 | 71848 | 112068 | 3.309 |
| 3 | 18654 | 37899 | 55697 | 2.032 |
| 4 | 19121 | 35770 | 50672 | 1.871 |
| 5 | 26113 | 42754 | 59296 | 1.637 |
| 6 | 13897 | 28978 | 47896 | 2.085 |
| 7 | 36590 | 65790 | 96011 | 1.798 |
| 8 | 44683 | 267851 | 696892 | 5.994 |
| 9 | 62957 | 103829 | 150946 | 1.649 |
| 10 | 100540 | 195903 | 363057 | 1.948 |
| 11 | 106321 | 252572 | 573812 | 2.332 |
| 12 | 53851 | 87600 | 127537 | 1.627 |
| 13 | 32209 | 86289 | 153172 | 2.741 |
| 14 | 26140 | 137384 | 256857 | 5.256 |
| 15 | 17724 | 120777 | 247683 | 6.814 |
| 16 | 6840 | 7774 | 8798 | 1.137 |
| 17 | 6817 | 8085 | 9457 | 1.186 |

Example 7

Polymerization of 2-(2-Methoxy-4-vinyl-phenoxymethyl)-oxirane

Into a 25 mL Schlenk tube was added 2.06 g of 2-(2-Methoxy-4-vinyl-phenoxymethyl)-oxirane (prepared as described in example 5), 3.1 ml of THF, 9.3 mg of VAZO 64(AIBN), and 55.7 mgs of RAFT agent (as in Example 6). The reaction mixture was then freeze thaw degassed. The reaction mixture was then heated overnight at 68° C. for ~16 h. The progress was measured by sampling the reaction, removing solvent and running 1H NMR which showed monomer present. An extra 9.3 mgs of VAZO 64 in 0.1 mL of THF was added and the mixture heated for 4 h. The sampling procedure was then repeated and an additional 9.3 mg of VAZO 64 in 0.1 mL of THF was added and heating continued overnight. The reaction mixture was cooled to RT, and ~1 ml of THF was added, then the mixture was poured into 150 mL of petroleum ether. A yellow solid precipitated and was collected by filtration, then washed with fresh pet ether to give 2.01 g of yellow solid. 1H NMR in CD2Cl2 showed expected resonances. Mol. Wt. by GPC was obtained: Mw=8366 and Mn=7004.

What is claimed is:

1. A method for the synthesis of a glycidyloxystyrene monomer or a substituted glycidyloxystyrene monomer comprising the steps of:

a) providing a phenolic substrate having the general structure:

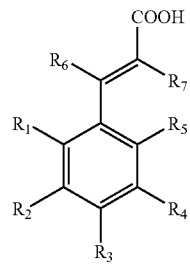

wherein $R_1$, $R_2$, $R_3$, $R_4$, and $R_5$ are H, OH, OCH$_3$, OR$_8$, or linear or branched alkyl, aryl, halo, or cyano; $R_6$ and $R_7$ are H, halo, or cyano;

$R_8$ is linear or branched alkyl or aryl; provided that at least one of $R_1$, $R_3$, or $R_5$ is OH;

b) providing a reaction mixture comprising:
  i) a non-amine basic catalyst; and
  ii) at least one aprotic, polar solvent;

c) contacting the phenolic substrate of (a) with the reaction mixture of (b) at a temperature of at least about 100° C. for a time sufficient for the decarboxylation of the phenolic substrate to a decarboxylated product;

d) contacting the decarboxylated product of (c) with a halomethyl-oxirane and a basic catalyst at a temperature between about 20° C. and about 120° C. for a time sufficient for glycidyloxystyrene monomer or substituted glycidyloxystyrene monomer synthesis; and e) optionally recovering the glycidyloxystyrene monomer or substituted glycidyloxystyrene monomer.

2. A method for the synthesis of homopolymers and copolymers of glycidyloxystyrene monomer or substituted glycidyloxystyrene monomer comprising:

a) providing a phenolic substrate having the general structure:

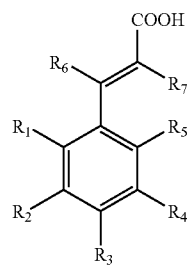

wherein $R_1$, $R_2$, $R_3$, $R_4$, and $R_5$ are H, OH, OCH$_3$, OR$_8$, or linear or branched alkyl, aryl, halo, or cyano; $R_6$ and $R_7$ are H, halo, or cyano;

$R_8$ is linear or branched alkyl or aryl; provided that at least one of $R_1$, $R_3$, or $R_5$ is OH;

b) providing a first reaction mixture comprising:
  i) a non-amine basic catalyst; and
  ii) at least one aprotic, polar solvent;

c) contacting the phenolic substrate of (a) with the reaction mixture of (b) at a temperature of at least about 100° C. for a time sufficient for the decarboxylation of the phenolic substrate to a decarboxylated product;

d) contacting the decarboxylated product of (c) with a halomethyl-oxirane and a basic catalyst at a temperature between about 20° C. and about 120° C. for a time sufficient for glycidyloxystyrene monomer or substituted glycidyloxystyrene monomer synthesis;

e) optionally recovering the glycidyloxystyrene monomer or substituted glycidyloxystyrene monomer; and f) reacting the glycidyloxystyrene monomer or substituted glycidyloxystyrene monomer, with a second reaction mixture comprising:
1) optionally at least one co-monomer; and
2) a polymerization initiator;
at a temperature and time sufficient to produce a glycidyloxystyrene homopolymer or copolymer, or substituted glycidyloxystyrene homopolymer or copolymer.

3. A method according to claim 1 or 2 wherein $R_3$ is OH.

4. A method according to claim 1 or 2 wherein the phenolic substrate is selected from the group consisting of 4-hydroxycinnamic acid, ferulic acid, sinapinic acid, caffeic acid, 2-hydroxycinnamic acid, and α-cyano-4- hydroxycinnamic acid.

5. A method according to claim 1 or 2 wherein the non-amine basic catalyst comprises potassium.

6. A method according to claim 1 or 2 wherein the non-amine basic catalyst is an acetate salt.

7. A method according to claim 1 or 2 wherein the non-amine basic catalyst is a metallic salt.

8. A method according to claim 1 or 2 wherein the non-amine basic catalyst is selected from the group consisting of potassium acetate, potassium carbonate, potassium hydroxide, sodium acetate, sodium carbonate, sodium hydroxide and magnesium oxide.

9. A method according to claim 1 or 2 wherein the non-amine basic catalyst is at a concentration of about 1 mol % to about 30 mol % relative to the phenolic substrate in the reaction mixture.

10. A method according to claim 1 wherein the at least one aprotic, polar solvent is selected from the group consisting of N,N-dimethylformamide, 1-methyl-2-pyrrolidinone, N,N-dimethylacetamide, dimethylsulfoxide, hexamethylphosphoramide, and hexamethylphosphorous triamide.

11. A method according to claim 10 wherein the solvent is N,N-dimethylformamide or N,N-dimethylacetamide.

12. A method according to claim 1 or 2 wherein a polymerization inhibitor is included at any step.

13. A method according to claim 12 wherein the polymerization inhibitor is selected from the group consisting of hydroquinone, hydroquinone monomethylether, 4-tert-butyl catechol, phenothiazine, N-oxyl (nitroxide) inhibitors, 4-hydroxy-TEMPO (4-hydroxy-2,2,6,6-tetramethylpiperidin-1-yloxy, CAS#2226-96-2) and 1,6-hexamethylene-bis(N-formyl-N-(1-oxyl-2,2,6,6-tetramethylpiperidine-4-yl) amine).

14. A method according to claim 1 or 2 wherein a polymerization retarder is included at any step.

15. A method according to claim 14 wherein the polymerization retarder is selected from the group consisting of dinitro-ortho-cresol (DNOC) and dinitrobutylphenol (DNBP).

16. A method according to claim 1 or 2 wherein the yield of glycidyloxystyrene monomer or substituted glycidyloxystyrene monomer product in (d) is at least about 48%.

17. A method according to claim 1 or 2 wherein the halomethyl-oxirane is epichlorohydrin, epibromohydrin or 2-(chloromethyl) 2-methyl oxirane.

18. A method according to claim 1 or 2 wherein (a)-(d) are performed in a single reactor vessel.

19. A method according to claim 2 wherein the co-monomer of (f) is selected from the group consisting of styrene or substituted styrenes; acrylates; methacrylates or dimethacrylates; fluorine-containing compounds; acrylic acid; methacrylic acid; maleic acid; fumaric acid; maleic anhydride; acrylonitrile; acrylamides; methacrylamides and mixtures thereof.

* * * * *